(12) United States Patent
Kulkarni et al.

(10) Patent No.: US 7,531,612 B2
(45) Date of Patent: May 12, 2009

(54) PH SENSITIVE POLYMER AND PROCESS FOR PREPARATION THEREOF

(75) Inventors: Mohan G. Kulkarni, Maharashtra (IN); Anupa R. Menjoge, Maharashtra (IN)

(73) Assignee: Council for Scientific and Industrial Research, New Delhi (IN)

( * ) Notice: Subject to any disclaimer, the term of this patent is extended or adjusted under 35 U.S.C. 154(b) by 720 days.

(21) Appl. No.: 10/738,949

(22) Filed: Dec. 19, 2003

(65) Prior Publication Data

US 2005/0137372 A1    Jun. 23, 2005

(51) Int. Cl.
*C08F 118/02* (2006.01)

(52) U.S. Cl. .................... 526/319; 526/324; 526/328.5; 526/329; 526/331

(58) Field of Classification Search ............... 526/319, 526/324, 328.5, 329, 331
See application file for complete search history.

(56) References Cited

U.S. PATENT DOCUMENTS

| | | | | |
|---|---|---|---|---|
| 4,996,243 A | * | 2/1991 | Rasmussen et al. | 522/99 |
| 6,797,768 B2 | * | 9/2004 | Lyons | 524/561 |

* cited by examiner

*Primary Examiner*—Robert D. Harlan
(74) *Attorney, Agent, or Firm*—Nixon & Vanderhye P.C.

(57) ABSTRACT

The present invention relates a novel pH sensitive polymer which exhibits pH dependant swelling/dissolution behavior. The composition is useful for taste masking of bitter drugs and also for the gastric delivery of the drugs. The said polymer comprises a hydrophobic monomer polymerized along with a basic monomer or a hydrophobic monomer polymerized along with a basic monomer and a hydrophilic monomer.

8 Claims, No Drawings

PH SENSITIVE POLYMER AND PROCESS FOR PREPARATION THEREOF

FIELD OF INVENTION

The present invention relates to pH sensitive polymers, which swell and/or solubilize in acidic pH≦3 as found in the stomach and remain deswelled or insoluble in the pH>3.5 normally the pH of the pharmaceutical liquid orals and also in the pH of saliva, and to a process for the preparation thereof.

BACKGROUND OF INVENTION

For more than two decades the delivery of bioactive agents from polymeric materials has attracted considerable attention of investigators working in the field of drug delivery systems. New technological advances have brought many innovative drug delivery systems to the market and others are close to commercialization. Polymers play an important role in the formulation of drug products. Polymer based excipients have been used in formulations for a variety of reasons, including taste masking, protection and stabilization of the drug, etc. The synthetic and naturally occurring polymers are being used in the form of matrix, hydrogels, microparticles, nanoparticles, films and sponges in the drug delivery system. The applications of polymers either synthetic or natural are continuing and increasing in the field of formulations of drugs. Many of the polymers are used in the oral delivery of the drugs either for film coating of the tablets or for the modified release of the drugs from the delivery systems. The choice of polymers for the investigators working in the field of the advanced drug delivery systems are severely limited by the candidate polymeric materials as evidenced by the relatively small number of polymeric materials available commercially in comparison to the number of drugs marketed.

Some of the synthetic polymers commercially available include cellulose derivatives like ethyl cellulose, cellulose acetate, cellulose acetate phthalate and acrylic acid and methacrylic acid polymers like Carbopol and Eudragit. The barrier coating of bitter drug with the various polymers is extensively used for taste masking of the drugs especially when the formulation is to be administered in the form of a liquid oral like the suspension or dry syrup. Taste masking is very important when the drug is extremely bitter. Perception of bitter taste makes the preparation unacceptable or unpalatable. Bitter taste of drugs that are orally administered is disadvantageous in several aspects. Taste is an important parameter governing compliance. The disagreeable taste of drugs causes difficulties in swallowing or causes patients to avoid their medication thereby resulting in low compliance of patients. Conventional taste masking techniques such as use of sweeteners, amino acids, flavoring agents are often inadequate in masking taste of highly bitter drugs like quinine, barberin, celecoxib, etoricoxib, antibiotics like levofloxacin, ofloxacin, sparfloxacin, ciprofloxacin, cefuroxime axetil, erythromycin and clarithromycin. Thus taste-masking technologies are considered important and developed by many researchers.

Japanese Patent Application JP 2003231647 A2 discloses an oral liquid preparation comprising fruit type flavors and sweeteners like acesulfame to mask the unpleasant taste or odor of pharmaceutical and food components. Japanese Patent Application JP 2001106641 discloses a chewable tablet wherein the bitter taste of the active ingredient is masked by the addition of the sugar alcohol like xylitol, a coolant like menthol and hard fat.

Although sweeteners and flavors were used for taste masking, this alone was not sufficient for taste masking of highly bitter drugs and use of polymeric materials was mostly favored and many efforts have been made to taste mask drugs using polymeric materials.

U.S. Pat. No. 6,514,492 discloses a liquid oral formulation of quinolones comprising ion exchange resins, such as methacrylic acid polymer crosslinked with divinylbenzene, for elimination of extreme bitterness of the quinolones. Patent Application WO 03/06066 A1 discloses ternary ionic complexes which have a pleasant taste. The complexes are used for liquid suspension dosage forms for the children. A complex is formed using an active ingredient with an ionisable cationic group and a charged polymer with an anionic group and a polymer with cationic charge.

A fast dissolving orally consumable film comprising a film forming polymer and ion exchange resin is disclosed in Patent Application WO 01/70194. The taste masking is achieved by the use of sulfonated polymer ion exchange resin comprising polystyrene cross-linked with divinylbenzene, such as Amberlite™. The taste masked antitussive film of dextromethorphan using amberlite and film forming polymers like xanthan gum, locust bean gum, carrageenan and pullulan is disclosed.

Patent Application WO 02/72111 discloses a taste masked pharmaceutical suspension comprising the antibiotic telithromycin which is coated by a waxy material like glyceryl monostearate and optionally by a binding agent or a polymer like Eudragit E. Granules and granules coated with a masked taste are disclosed in the patent application WO 02/72072. A bitter active ingredient like clarithromycin, coated by a waxy compound like gelucire and a polymer like eudragit E is disclosed. Japanese Patent Application JP 2001-172201 discloses a taste masking coating composition comprising polyvinyl acetate, hydrophilic additives and other conventional coating agents like kollidion and propylene glycol. Coated ibuprofen is compressed into chewable tablets.

Patent Application WO 00/18372 discloses grains obtained by spray solidification of drug, clarithromycin, glycerine fatty acid ester and an enteric or gastric polymer. The gastric polymer used for the taste masking was Eudragit E. A taste masked pharmaceutical composition containing acrylic polymeric coatings is disclosed in Patent Application WO 0269939.The microcapsules of the drug levofloxacin, were coated by the water-insoluble enteric coating, comprising methacrylic acid-Et acrylate copolymer, are disclosed.

Patent Application WO 01/80829 discloses the taste masking coating compositions containing polymers comprising polyvinyl acetate, and a dimethylaminoethyl methacrylate and neutral methacrylic acid ester. In addition to the polymers an alkali modifier may be added to the coating composition to enhance the release of the active agent. The coated granules are compressed into tablets. Patent Application WO 01/80826 discloses a coating composition based on the methacrylate polymer and the cellulose ester, which masks the undesirable taste of the pharmaceutically active agent like acetaminophen. The coating composition comprises dimethylaminoethyl methacrylate and neutral methacrylic acid ester polymer (Eudragit E 100), and a cellulose ester polymer (cellulose acetate).

The taste-masked pharmaceutical composition containing histamine H2 antagonist in the form of chewable tablets is disclosed in U.S. Pat. No. 6,270,807. The histamine H2 antagonist, famotidine was coated by a composition comprising water-insoluble component glyceryl monostearate and water-permeable methacrylate ester copolymer Eudragit NE30D to provide a taste-masking effect for a relatively short period when the compound is being chewed by a patient.

Patent Application WO 01/35930 discloses taste masked oral compositions based on polyacrylates. The effective taste masking of the active pharmaceutical like ciprofloxacin by granulation with aqueous solution of neutral methacrylic acid ester is disclosed. Patent Application WO 01/03698 discloses polymer blends for taste masking of the pharmaceutical liquid formulations. The pharmaceutically active drugs like antibiotics, analgesics, anti-inflammatory drugs, gastrointestinal drugs, antihistamines, decongestants, antidepressants, antipsychotics, antivirals, oncolytics, vaccines, antiepileptics, antiasthma drugs, and antispasmodics, are coated with effective amount of a polymer blend of (a) dimethylaminoethyl methacrylate and neutral methacrylic acid ester (MM/MAE) like Eudragit E and (b) a cellulose ester like cellulose acetate in an aqueous vehicle. The polymer coating masks the taste of the composition comprising levofloxacin.

Taste masking, rapid release coating systems are disclosed in the patent application WO 00/30617. The drug core of dextromethorphan is encased in the spacing layer comprising of ethyl cellulose and polyvinyl pyrrolidone and a taste masking layer comprising of Eudragit E. The resulting beads are taste less for approximately 30 seconds. European Patent EP 1279402 A1 discloses orodispersible tablets comprising of the allyamine or benzylamine or the salts e.g. terbinafine hydrochloride in the form of coated granules where the granules are coated by cellulose derivatives like hydroxypropyl methylcellulose, povidones, polyvinyl alcohols and further by ethyl cellulose and acrylic polymers. US Patent Application 2002-132006 A1 discloses an odor and taste masking coating comprising of hydroxyalkyl cellulose, an antitackiness agent and a methacrylate copolymer.

Patent Application WO 03/00225 A2 discloses a suspension formulation, which comprises of the taste masked powder of the active ingredient comprising a cellulose polymer and a methacrylic polymer along with alkaline agent and a adsorbing agent. US Patent Application 2002-197317 A1 discloses a coating composition containing polymer comprising dimethylaminoethyl methacrylate and neutral methacrylic acid ester, a cellulose ester polymer, and an alkaline modifier, which masks taste of the active ingredient.

A taste masked pharmaceutical particles containing a polymeric coating is disclosed in Patent Application EP 1166777. Taste masked particles are further formulated into chewable tablets. The core containing the active agent ibuprofen is coated by a enteric polymer and film forming polymer e.g. hydroxypropyl methyl cellulose phthalate and cellulose acetate. Coated particles are blended with other agents such as sweeteners like acesulfame, aspartame, citric acid, mannitol and flavoring agent and then compressed into chewable tablets. Patent Application WO 02/87622 A1 discloses an oral film preparation comprising a drug containing layer and two water swelling gel forming layers. Polymers such as polyacrylic acid and hydroxypropyl cellulose are used in the formulation. Texture masked particles coated by the film-forming polymer and anti grit agent are disclosed in Patent Application EP 1219291.Texture masked particles are formulated into the chewable tablets. The texture masking effect is achieved by coating the core comprising of acetaminophen and ethyl cellulose with hydroxypropyl methylcellulose. Japanese Patent Application JP 2002-292344 discloses film coating agents, which have higher taste masking effect and exhibit desirable drug release. The film coating agents comprise a dispersion of Eudragit NE 30 D (Ethyl acrylate-methyl methacrylate copolymer) and methylcellulose.

Patent Application JP 2000128776 discloses film coated pharmaceutical granules wherein the film coating comprises of aqueous dispersion of ethyl cellulose, Aquacoat ECD 30 and Eudragit NE 30 D (ethyl acrylate-methyl methacrylate copolymer emulsion.) The drug is released in 5, 10, and 20 min from the composition.

Taste masked pharmaceutical particles containing the polymeric coating are disclosed in Patent Application EP 1166777. The drug particles are taste masked using the polymeric coating which comprises a mixture of enteric polymer hydroxypropyl methyl cellulose phthalate and an insoluble film forming polymer, cellulose acetate. Patent Application JP 2000-053563 discloses the taste masked granular composition comprising the coating layer of ethyl cellulose to mask the bitter taste. Use of gastric soluble polymers for unpleasant taste masking is disclosed in JP 11228393. The polymers used for the coating comprise polyvinyl acetal diethylaminoacetate.

Use of cationic polymers comprising dimethylaminoethyl methacrylate and neutral methacrylic acid esters marketed as Eudragit E is disclosed in Patent Application WO 99/17742. U.S. Pat. No. 5,837,277 discloses a palatable pharmaceutical composition containing acrylic polymers. Acrylic polymers are used to taste mask the anti-inflammatory drug. Acrylic polymers used comprise copolymers of poly (Ethyl acrylate, Methyl methacrylate) in which quaternary ammonium groups have been introduced to modify the permeability of the ester marketed under the name Eudragit RL 30D and Eudragit RS 30D.

The following patents and patent applications disclose the use of polymers for the taste masking application of the drugs: WO 00/06122 A1; JP 2000-007557 A2; JP 2000-007556 A2; EP 943341; WO 98/47493; WO 98/30209; WO 98/14179; WO 97/41839; WO 97/09967; WO 96/34628; EP 724880; WO 96/10993; EP 706821; WO 95/15155; JP 07076517; WO 95/05166; WO 94/27596; WO 94/12157; WO 94/05260; WO 93/24109; JP 05255075; WO 93/17667; JP 91-298966; JP 05201855; EP 523847

Patent Application WO 00/56266 discloses the use of a high viscosity swellable polymer carbomer, in combination with film forming polymethacrylates and channelising agents for taste masking of bitter drugs. The addition of the water swellable polymer aids in the fast release of the active ingredient in the gastric media. Patent Application WO 00/76479 discloses a taste masking composition, using a combination of two enteric polymers comprising methacrylic acid copolymer and a phthalate polymer. This application discloses the use of channelising agents, which comprise water soluble or water swellable materials to aid release of active ingredient. The enteric polymers as disclosed in the patent are known to release the active ingredient at alkaline pH where the polymers are soluble. The release of the active ingredient will be delayed due to the use of the enteric polymers and in case of the medicaments having a narrow absorption window limited to upper gastrointestinal tract; such system would be of limited use.

Microencapsulation of highly bitter drug cefuroxime axetil for taste masking is disclosed by M.Cuna et.al (M. Cuna, M. L. Lorenzo, J. L. Vila Jato, D. Torres, M. J. Alonso, Acta Technologiae et Legis Medicamenti. volume VII, N.3, 1996) using different polymeric materials like cellulose acetate trimellitate, HPMCP-50, HPMCP-55 with the final aim to mask the taste and assuring its release in the intestinal cavity. Alonso et al (M. J. Alonso, M. L Lorenzo-Lamosa, M.Cuna, J. L. Vila-Jato and D. Torres, Journal of Microencapsulation, 1997, Volume 14, No.5, 607-616) describe the encapsulation of cefuroxime axetil, a highly bitter drug, in pH sensitive acrylic microspheres in order to formulate a suspension dosage form. The acrylic polymers used were eudragit E, eudragit RL 100, eudragit L100-55. The cationic Polymer eudragit E showed a negative interaction with cefuroxime axetil. The enteric polymer eudragit L100-55 showed a favorable release in alkaline pH.

In the above disclosures the release of cefuroxime axetil was studied in the basic media whereas Dantzig et al (Anne H. Dantzig, Dale C. Duckworth, Linda B. Tabas, Biochimica et Biophysica Acta 1191, 1994, 7-13) showed that cefuroxime axetil is hydrolyzed to cefuroxime in the intestinal lumen by the esterases, reducing cefuroxime axetil concentration in the lumen and resulting in reduced absorption, resulting in lower bioavailability of Cefuroxime axetil in humans. Cefuroxime axetil already has a low bioavailability of 32-50% and hence a further reduction in the bioavailability due to the formulation aspects should be minimized. The optimum conditions for the spray congealing of the bitter drug clarithromycin using the mixture of the wax: glyceryl monostearate and a polymer: aminoalkyl methacrylate copolymer E (AMCE). (Yajima, Toshio; Umeki, Nobuo; Itai, Shigeru. Chemical & Pharmaceutical Bulletin (1999), 47(2), 220-225) are discussed It is evident from the above disclosures, that taste masking can be achieved by various methods. Many natural and synthetic polymers, resins and waxes alone or in combination have been employed for taste masking. The enteric polymers like eudragit L are used for taste masking but the pH of saliva is near 5.8 and these polymers solubilize at pH beyond 5.5 so there is a possibility of drug being partially leached. Therefore there is a need for the development of taste masking polymer such that the bitter taste is completely masked by the polymer at the pH of saliva in mouth and in the reconstitution medium as in case of the liquid orals and further which is able to protect the drug in a biologically active form, from the moisture in the dosage form and releasing the drug rapidly in the stomach without affecting its absorption and bioavailability.

Most of the references described above, describe compositions, which satisfactorily mask the bitter taste of the medicament in the pharmaceutical compositions but cannot release the drug in gastric cavity immediately after ingestion without affecting the bioavailability. Further the polymers like ethyl cellulose, eudragit RS and RL would take some time to release the drug and enteric polymers like cellulose acetate phthalate, hydroxypropyl methylcellulose phthalate, eudragits like L 100 would delay the release of the drug till it reaches the small intestine. Hence such polymers might not be of use when the drug has to be absorbed immediately without, any delay or has an absorption window restricted to the upper gastric region. Thus there is a need to develop a polymer, which is effective in taste masking of the drug but does not cause a delay in the release of the drug.

Whilst the use of polymer coating as mentioned in the above examples may be effective for retarding dissolution of the drug during the time in contact with saliva, during the process of swallowing, it has disadvantages in preparing taste masked liquid formulations intended for long term storage in contact with liquid medium.

A large number of polymers, which exhibit pH dependant dissolution behavior, have been reported in literature. Polymers containing carboxylic functional groups as well as cellulose derivatives are known to dissolve at pH above 5.5. However, these polymers are not useful for taste masking, as they would dissolve at pH of saliva and at pH of reconstitution medium. Further these polymers will not release the encapsulated drug in the stomach since these polymers do not dissolve or swell sufficiently at pH prevalent in the stomach.

Polymers containing basic functional groups such as amino groups are known to dissolve at pH prevalent in the stomach. Such polymers are referred to as reverse enteric coatings. The polymer eudragit E marketed by Rohm and Haas belongs to this category. (Eudragit E, Technical literature Rohm and Haas). These polymers also show swelling at pH 5 and hence will release the drug at the pH of the saliva as well as the reconstitution medium and will not be useful for taste masking. There is therefore a need for the developing pH sensitive polymer compositions, which will exhibit very specific pH dependant behavior. The polymeric compositions disclosed in this invention exhibit specific pH dependent dissolution behavior and are not reported in the literature in the past.

Regardless of the numerous techniques and pharmaceutical adjuncts known in the art to mask the taste of bitter-tasting medicaments, there remains the need to find an effective technique, adjunct or combination thereof for specific agents.

OBJECTS OF THE INVENTION

It is an object of the invention to provide pH sensitive polymers for use in pharmaceutical applications such as the delivery of the drugs in the gastric region.

It is another object of the invention to provide pH sensitive polymer, which swells or solubilizes at the acidic pH of stomach and can release the drug almost immediately in the gastric region, without causing any delay.

It is yet another object of the invention to provide a pH sensitive polymer which releases drug in gastric region almost immediately, resulting in no alteration in bioavailability of drugs that have a narrow absorption window restricted to upper gastric region.

It is another object of the invention to provide a pH sensitive polymer that can be used in a variety of dosage forms like film coating of the tablets, coating of bitter particles of the drugs to be formulated as dry syrups, suspension and chewable or rapidly disintegrating tablets where taste masking is required.

It is another object of the invention to provide pH sensitive polymers that provide a moisture barrier to sensitive moieties being insoluble in water and hydrophobic in nature.

SUMMARY OF THE INVENTION

Accordingly the present invention provides for a new polymer which exhibits pH dependent swelling/dissolution behavior, having the formula $P[A_{(x)}B_{(y)}C_{(z)}]$ wherein P is a pH sensitive polymer comprising (A) a hydrophobic monomer, (B) a basic monomer and (C) a hydrophilic monomer and (x)=30-95%, (y)=5-70%, (z)=0-60%, all percentages expressed in terms of w/w.

In one embodiment of the invention the hydrophobic monomer (A) comprises a acrylic and methacrylic acid ester selected from the group consisting of cyclohexyl acrylate, dodecyl acrylate, 2 ethyl hexyl acrylate, octyl acrylate, tertiary butyl acrylate, phenyl acrylate, butyl acrylate, methyl methacrylate, benzyl methacrylate, cyclohexyl methacrylate, phenyl methacrylate, tertiary butyl methacrylate, butyl methacrylate, 2 ethyl hexyl methacrylate, propyl methacrylate preferably butyl acrylate, methyl methacrylate and butyl methacrylate.

In another embodiment of the invention, the basic monomer (B) is selected from the group consisting of a amino alkyl acrylic acid and a methacrylic acid esters.

In yet another embodiment of the invention, the basic monomer (B) is selected from the group consisting of dimethyl amino ethyl methacrylate, dimethyl amino ethyl acrylate, diethyl amino ethyl methacrylate, diethyl amino ethyl acrylate, piperidine ethyl methacrylate, 2 tert-butyl amino ethyl methacrylate, preferably dimethyl amino ethyl methacrylate and diethyl amino ethyl acrylate In still another embodiment of the invention the basic monomer (B) is an alkenyl pyridine is selected from the group consisting of 2 vinyl pyridine, 3-vinyl pyridine, 4 vinyl pyridine and 5 vinyl 2 picoline, 2-vinyl 4 picoline, 2 isopropenyl pyridine and 3 isopropenyl pyridine, preferably 4 vinyl pyridine.

In still another embodiment of the invention the basic monomer (B) is selected from the group comprising of vinyl quinolines, amino alkyl vinyl ethers, amino ethyl styrenes and allylic amine, preferably allylic amines.

In yet another embodiment of the invention the hydrophilic monomer (C) is a acrylic or methacrylic acid ester is selected from the group consisting of hydroxy ethyl methacrylate, hydroxy propyl methacrylate, hydroxyethyl ethyl methacrylate, hydroxy ethyl acrylate, hydroxy propyl acrylate, hydroxyethyl ethyl acrylate preferably hydroxy ethyl methacrylate and hydroxyethyl ethyl methacrylate.

In another embodiment of the invention, the pH sensitive polymer has a molecular weight range of 1000 to 7,00,000.

In still another embodiment the pH sensitive polymer solubilizes or swells in the acidic pH$\leq$3 as found in stomach and remains insoluble or de swelled in the pH range>3.5

The present invention also relates to a process for the preparation of a polymer which exhibits pH dependent swelling/dissolution behavior, having the formula $P[A_{(x)}B_{(y)}C_{(z)}]$ wherein P is a pH sensitive polymer comprising (A) a hydrophobic monomer, (B) a basic monomer and (C) a hydrophilic monomer and (x)=30-95%, (y)=5-70%, (z)=0-60%, all percentages expressed in terms of w/w, the process comprising polymerising a mixture of the hydrophobic and basic monomer or a mixture of the hydrophobic, hydrophilic and basic monomer.

In one embodiment of the invention the pH sensitive polymer is synthesized by conventional techniques known in the art selected from bulk, solution, emulsion or dispersion polymerisation preferably by bulk or solution polymerisation.

In one embodiment of the invention, the polymerisation is carried out by bulk polymerisation wherein the hydrophobic and basic monomer or hydrophobic, hydrophilic and basic monomers are polymerized in the presence of a free radical initiator.

In another embodiment of the invention, the polymerisation is carried out by solution polymerisation comprising dissolving the hydrophobic and basic monomer or hydrophilic, hydrophobic, and basic monomer in a solvent and subjecting the solution to polymerisation.

In a preferred embodiment of the invention, the solvent used for the polymerization is any solvent in which the monomers are soluble and is selected from a aromatic hydrocarbon, chlorinated hydrocarbon, alcohol, ester, ketone, formamide, tetrahydrofuran, dioxane and dimethyl sulfoxide preferably a formamide such as dimethyl formamide.

In a still preferred embodiment of the present invention the % weight of solvent to the monomer during the synthesis of the pH sensitive polymer is 20 to 100 preferably 30 to 80.

In yet another embodiment of the present invention the bulk or solution polymerization of the hydrophobic and basic monomer or hydrophobic, hydrophilic and basic monomer to yield the pH sensitive polymer is carried out in presence of a free radical initiator wherein the free radical initiator used for polymerisation comprises compounds such as azocompounds, peroxides, hydroperoxides, peracids and peresters preferably azocompounds.

In a further embodiment of the present invention the azo initiator comprising of azo-bis-cyano valeric acid, azo-bis-diphenyl methane, azo-bis-methyl isobutyrate and azo-bis-isobutyronitrile preferably azo-bis-isobutyronitrile is used for polymerization.

In the preferred embodiment of the present invention, the % weight of initiator to monomer in the polymerization being 0.1 to 5 preferably 0.2 to 3.

In another embodiment of the invention the polymerisation is carried out at temperature 50-80° C. for a period of 15-18 hours.

DETAILED DESCRIPTION OF THE INVENTION

This invention relates to the synthesis of pH sensitive polymers, which can be used for the pharmaceutical applications. With the advances in polymer chemistry, new applications are developed for the polymers. Polymers are being tested for various applications like formulations and drug delivery systems. Polymers play an important role in the formulation of drug products. Polymer based excipients have often been used in formulations for a variety of reasons, including taste masking, protection and stabilization of the drug, The enteric polymers like cellulose derivatives and Eudragit series are used for the taste masking applications. The polymer Eudragit E is most commonly used polymer for the taste masking of the drugs however certain bitter drugs like cefuroxime axetil, showed a negative interaction with the cationic polymer eudragit E. (M. J. Alonso, M. L Lorenzo-Lamosa, M.Cuna, J. L. Vila-Jato and D. Torres, Journal of Microencapsulation, 1997, Volume 14, No.5, 607-616). Further Eudragit E (a Dimethyl amino Ethyl Methacrylate copolymer) available from Rohm GmbH, Darmstadt, Germany is insoluble in the basic pH, however it is found that the polymer shows some swelling in the neutral to slightly acidic pH which may cause a problem if the liquid orals are to be formulated at that pH. The pH sensitive polymer as disclosed in the present invention shows a swelling or solubilization in the acidic pH$\leq$3. The pH sensitive polymer further remains deswelled or insoluble in the pH>3.5. Further the pH sensitive polymer does not show the negative interaction between the drug and the polymer. The pH sensitive polymer disclosed in the present invention can be applied in the various pharmaceutical dosage forms where the polymer is required to be solubilized in the stomach without causing any delay in the release of the drug. The polymers can be of use in the taste masking of the immediate release tablets by film coating and also in case of chewable and rapidly disintegrating tablets, since the polymer does not solubilize at the pH of the saliva. More particularly the pH sensitive polymer as disclosed in the present invention can be used in the taste masking of the bitter drugs which need to administered in the form of dry syrups and suspensions wherein the polymer is expected to prevent the leaching of the drug in the reconstituted medium for the entire period of storage and also release the drug immediately in the stomach without causing any delay. The use of pH sensitive polymer, which is disclosed in the present invention with gastric solubility would therefore not cause any change in the bioavailability of the drugs, which have a narrow absorption window particularly limited to the upper gastric region.

The polymers covered by the present invention can be synthesized by any polymerization techniques like bulk polymerization, solution polymerization, suspension polymerization and emulsion polymerization. The pH sensitive polymer of the present invention having the desired pH sensitive characteristics can be obtained by varying the composition of monomers essentially comprising of the hydrophobic monomer and basic monomers and optionally hydrophilic monomers, such that the pH sensitive polymers exhibit required swelling and deswelling characteristic at the acidic and neutral and near neutral pH. The stimuli sensitive polymer of the present invention has the monomeric composition such that it either swells or solubilizes in the acidic pH of $\leq 3.0$ and does not solubilize or swell or swells marginally in the pH>3.5 making them most suitable for the pharmaceutical application like taste masking.

The hydrophobic monomer is selected from the group consisting of acrylic and methacrylic acid esters like cyclohexyl acrylate, dodecyl acrylate, 2 ethyl hexyl acrylate, octyl acrylate, tertiary butyl acrylate, phenyl acrylate, butyl acrylate, methyl methacrylate, benzyl methacrylate, cyclohexyl methacrylate, phenyl methacrylate, tertiary butyl methacrylate, butyl methacrylate, 2 ethyl hexyl methacrylate, propyl methacrylate preferably butyl acrylate, methyl methacrylate and butyl methacrylate. In a still preferred embodiment of the present invention the basic monomer is selected from the group consisting of amino alkyl acrylic acid and methacrylic acid esters like dimethyl amino ethyl methacrylate, dimethyl amino ethyl acrylate, diethyl amino ethyl methacrylate, diethyl amino ethyl acrylate, piperidine ethyl methacrylate, 2 tert-butyl amino ethyl methacrylate, preferably dimethyl amino ethyl methacrylate and diethyl amino ethyl acrylate The basic monomer is selected from the group of alkenyl pyridines like 2 vinyl pyridine, 3- vinyl pyridine, 4 vinyl pyridine and 5 vinyl 2 picoline, 2-vinyl 4 picoline, 2 isopropenyl pyridine, 3 isopropenyl pyridine, preferably 4 vinyl pyridine. In still another embodiment of the present invention the basic monomer is selected from the group comprising of vinyl quinolines, amino alkyl vinyl ethers, amino ethyl styrenes and allylic amine, preferably allylic amines.

The hydrophilic monomer preferably consists of acrylic or methacrylic acid esters like hydroxy ethyl methacrylate, hydroxy propyl methacrylate, hydroxyethyl ethyl methacrylate, hydroxy ethyl acrylate, hydrox propyl acrylate, hydroxyethyl ethyl acrylate preferably hydroxy ethyl methacrylate and hydroxyethyl ethyl methacrylate.

The pH sensitive polymer can be synthesized by bulk polymerization, solution polymerization, suspension polymerization and emulsion polymerization preferably bulk or solution polymerisation. In bulk polymerization the hydrophobic, basic and optionally the hydrophilic monomers are taken in liquid state and initiator is dissolved in the monomer. The whole system is a homogeneous phase and is heated for initiating the polymerization.

The free radical initiator used for the synthesis of the pH sensitive polymer is chosen from a family of compounds comprising of azocompounds, peroxides, hydroperoxides, peracids and peresters. The synthesis of pH sensitive polymer is carried out in the presence of the azo initiator comprising of azo-bis-cyano valeric acid, azo-bis-diphenyl methane, azo-bis-methyl isobutyrate and azo-bis-isobutyronitrile. The preferred azo initiator for the polymerization reaction of the present invention is azo bis isobutyronitrile.

pH sensitive polymers can be synthesized by solution polymerization. Solution polymerization is advantageous where the polymer is to be used in solution form. In solution polymerization, monomers are dissolved in a suitable inert solvent optionally along with a chain transfer agent. A free radical initiator is also dissolved in the solvent medium. A preferred azo initiator for polymerization reaction of the invention is azo bis isobutyronitrile. Solvents in which monomers are soluble comprise of aromatic hydrocarbons, chlorinated hydrocarbons, alcohols, esters, ketones, formamides, tetrahydrofuran, dioxane and dimethyl sulfoxide. A solvent in which all the monomers are soluble freely is preferred. The preferred solvent used for solution polymerization is Dimethyl formamide. Solution polymerization in the present invention was carried out in dimethyl formamide, along with the free radical initiator azobisisobutyronitrile dissolving the hydrophobic, basic and optionally the hydrophilic monomer. Polymers synthesized by either bulk or solution polymerizations are recovered by dissolving in a solvent comprising dichloromethane and methanol in a ratio of 1:1. The polymer is precipitated from solution by precipitating in a nonsolvent like water, petroleum ether or diethyl ether and then dried under vacuum.

The pH sensitive behavior of the polymers synthesized was studied by carrying out the swelling study of the polymer films exposed to buffer solutions of different pH range. The films of the polymer synthesized were cast and pH dependant behavior of the polymer was studied to find the solublisation or swelling of the polymer in acidic medium and deswelling in the near neutral pH. Further the pH sensitive polymer synthesized is useful in taste masking of bitter drugs and for gastric delivery of drugs from the pharmaceutical dosage forms like microparticles, suspensions and tablets as the polymer is insoluble at the pH of saliva but solubilizes in the acidic pH$\leq 3$ as found in the stomach. pH sensitive polymers disclosed herein are useful for formation of drug delivery systems such as microparticles. The new polymer as disclosed forms a film and can be used for the formation of film coated drug delivery systems like film-coated tablets.

According to the basic feature of the present invention, a pH sensitive polymer which solubilizes or swells in the acidic pH of $\leq 3$ as found in the stomach is suitable for the taste masking of bitter drug wherein the polymer essentially solubilizes or swells in the acidic condition of the stomach and is capable of releasing the drug almost immediately. Further the pH sensitive polymer remains insoluble or deswelled in the pH range >3.5 making it more suitable for the application of taste masking as the bitter drug will not be released/leached by the polymer in the reconstitution or suspended medium in case of suspensions and also the drug will not be released from the polymer at the pH of the saliva as to give a perception of taste. Further the polymer shows a good film forming characteristics and such gastric soluble polymers can find the application in the film coating of the conventional pharmaceutical dosage forms which require a moisture barrier during storage period and release the drug almost without any delay in the stomach. The polymers as disclosed in the present invention are capable of making the pharmaceutical preparations more palatable since they remain deswelled in the pH>3.5 and swell or solubilize in the pH$\leq 3$.

Film casting of the polymer: A (12% w/v) solution of each polymer was prepared in the chloroform, and the resulting solution was spread uniformly on to horizontally supported flat surface of glass. The solvent was allowed to evaporate at room temperature. After the solvent had evaporated, the films were cautiously pulled off from the surface. Further the films were allowed to dry at room temperature. The swelling studies of the pH sensitive polymer were performed by placing films 25-36 sq. mm in size and 10-15 mg in weight in 15 ml of each of the above buffers separately in test tubes for each polymer. The changes in films in acidic pH 1.2, and in pH 4.5 and 5.8 were noted over a period of time.

Swelling study: To demonstrate the pH sensitive behavior of the polymers, swelling studies for the films of above polymers were conducted in buffer media of different pH. Swelling behavior of the polymers synthesized in example 1 and 2 is described in table 2 and 3. The swelling behavior of the polymers synthesized in the example 3 is described in table 4, 5 and 6. The swelling of polymers was calculated on the basis of the weight change of the film on exposure to the different media. The buffers used for the study were as follows:

Hydrochloric acid buffer pH 1.2: 0.1 N HCl was prepared by adding 425 ml of 0.2M HCl solution in distilled water to a 250 ml solution of (0.2M) potassium chloride in 1000 ml volumetric flask and the volume was made by distilled water.

Acetate buffer pH 2.8: Anhydrous sodium acetate 4.0 g was dissolved in 840 ml of distilled water and glacial acetic acid was added to adjust the pH to 2.8 and was diluted further with distilled water to make the volume to 1000 ml.

Citric acid buffer pH 4.5: For Citric acid buffer, 0.3 M (6.34 g in 100 ml distilled water) Citric acid and 0.03 M (9.5 g in 100 ml distilled water) Tri sodium Citrate solutions were prepared. The pH of the tri sodium citrate solution was adjusted to 4.5 by drop wise addition of Citric acid using pH meter.

Phosphate buffer pH 5.8: For Phosphate buffer 0.2 M NaOH and 0.2M Potassium dihydrogen phosphate, $KH_2PO_4$, solutions in distilled water were prepared. 250 ml of Potassium dihydrogen phosphate solution was taken and to this was added 18 ml of 0.2 M NaOH solution in distilled water to get the pH 5.8. Then the volume of this solution was made up 200 ml by distilled water.

EXAMPLE 1 pH sensitive polymers were synthesized by bulk polymerisation. Monomers methyl methacrylate 35% w/w, vinyl pyridine 30% w/w and hydroxyethyl methacrylate 35% w/w were mixed together and an azo initiator, azo bis isobutyronitrile 1% w/w of total monomer, was added. Reaction mixture was purged with nitrogen gas to provide inert atmosphere. Polymerization reaction was carried out by heating reaction mixture to 65° C. for a period of 18 hours. Polymer so synthesized was recovered by dissolving in solvent comprising dichloromethane and methanol (1:1) and precipitated in a nonsolvent. The nonsolvent used was diethyl ether. The polymer was dried at 27° C. under vacuum.

EXAMPLE 2

The pH sensitive polymer was synthesized by bulk polymerisation. The monomers methyl methacrylate 35% w/w, vinyl pyridine 30% w/w and Butyl acrylate 35% w/w were mixed together and an azo initiator, azo bis isobutyronitrile was added to 1% w/w of total monomer. The reaction mixture was purged with the nitrogen gas to provide the inert atmosphere. The polymerization reaction was carried out by heating the reaction mixture to 65° C. for a period of 18 hours. The polymer so synthesized was recovered by dissolving in solvent comprising dichloromethane and methanol 1:1 and precipitated it in a nonsolvent. The nonsolvent diethyl ether was used. The polymer was dried at 27° C. under vacuum.

TABLE 1

Swelling/Solubility behavior of polymers in Acidic buffer pH 1.2

| S.No | Polymer composition | Observed behavior |
|---|---|---|
| 1 | Methyl methacrylate 35% w/w Hydroxyethyl methacrylate 35% w/w Vinyl Pyridine 30% w/w | The polymer film started to dissolve immediately and the entire film solubilised in 10-15 min |
| 2 | Methyl methacrylate 35% w/w Butyl acrylate 35% w/w Vinyl Pyridine 30% w/w | The polymer film started to break in to pieces and went into solution in 45-50 min |

TABLE 2

Swelling/Solubility behavior of polymer in buffer of pH 5.8

| S.No | Polymer composition | Observed behavior |
|---|---|---|
| 1 | Methyl methacrylate 35% w/w Hydroxyethyl methacrylate 35% w/w Vinyl Pyridine 30% w/w | The polymer film did not show a swelling till 2 days and the swelling increased to 6.6% on day 7. |
| 2 | Methyl methacrylate 35% w/w Butyl acrylate 35% w/w Vinyl Pyridine 30% w/w | The polymer film showed a marginal swelling of 0.59% on day 2 and the swelling increased to 5.95% on day 7. |

EXAMPLE 3

The pH sensitive polymers were synthesized by solution polymerization. The hydrophobic monomer, basic monomer and optionally a hydrophilic monomer were dissolved in the solvent dimethyl formamide. An azo initiator, azobisisobutyronitrile was added to the monomer solution in dimethyl formamide. The reaction mixture was purged with nitrogen gas to provide inert atmosphere. Polymerization reactions were carried out by heating the reaction mixture to 65° C. for a period of 18 hours. The polymer so synthesized was recovered by dissolving in solvent comprising dichloromethane and methanol 1:1 and precipitation in a nonsolvent diethyl ether. Polymer was dried at 27° C. under vacuum. Polymers were characterized for molecular weight. Molecular weights of polymers synthesized were determined using Waters gel permeation chromatography and polystyrene standard (Polysciences Inc. USA) as reference using Styragel columns. Monomer composition of the polymers and molecular weights are summarized in Table 3.

TABLE 3

| S. No. | Polymer Composition | Monomer Weight % | Solvent[a] | Initiator[a] | Molecular Weight $M_w$ |
|---|---|---|---|---|---|
| 1. | MMA VP | 83 17 | 68.75 | 0.25 | 79,602 |
| 2. | MMA DMAEMA | 75 25 | 68.71 | 0.25 | 2,218 |
| 3. | BuMA VP | 60 40 | 55.44 | 0.25 | 1,14,393 |
| 4. | MMA HEMA VP | 52 37 11 | 70.86 | 0.5 | 1,57,226 |
| 5. | MMA HEMA DMAEMA | 50 37 13 | 69.06 | 0.25 | 52,370 |
| 6. | MMA HEMA PEMA | 39 23 38 | 62.09 | 0.5 | 13,152 |
| 7. | MMA BuMA VP | 41 32 27 | 43.54 | 0.25 | 33,788 |
| 8. | MMA BuMA DMAEMA | 49 34 17 | 44.29 | 0.25 | 1,86,456 |

TABLE 3-continued

| S. No. | Polymer Composition | Monomer Weight % | Solvent[a] | Initiator[a] | Molecular Weight $M_w$ |
|---|---|---|---|---|---|
| 9. | MMA | 39 | 43.47 | 0.25 | 51,611 |
|  | BuMA | 28 |  |  |  |
|  | PEMA | 33 |  |  |  |
| 10 | MMA | 47 | 72.64 | 0.5 | 59,966 |
|  | HEEMA | 32 |  |  |  |
|  | VP | 21 |  |  |  |
| 11 | MMA | 49 | 71.31 | 0.5 | 7,228 |
|  | HEEMA | 38 |  |  |  |
|  | DMAEMA | 13 |  |  |  |
| 12. | MMA | 49 | 70.70 | 0.5 | 14,589 |
|  | HEEMA | 27 |  |  |  |
|  | PEMA | 24 |  |  |  |

Where:
[a]% by weight of monomer
MMA = methyl methacrylate,
BuMA = butyl methacrylate,
DMAEMA = dimethyl aminoethyl methacrylate,
HEMA = hydroxy ethyl methacrylate,
VP = vinyl pyridine,
HEEMA = hydroxyethyl ethyl methacrylate,
PEMA = piperidine ethyl methacrylate

TABLE 4

Swelling/Solubility behavior of polymer in Acidic buffer pH 1.2

| Polymer No | Composition | Monomer w/w % | Observed behavior |
|---|---|---|---|
| 1. | MMA | 83 | The polymer film starts thinning from the sides and it almost completely solubilizes in 30 min with only a small part remaining which solubilizes in 60 min. |
|  | VP | 17 |  |
| 2. | MMA | 75 | The polymer film starts thinning and shows some swelling in 10 min and major portion solubilizes in 30 min and the remaining part in 60-80 min |
|  | DMAEMA | 25 |  |
| 3. | BuMA | 60 | The polymer film swells upto 30 min and then solubilizes almost completely in 45-50 min |
|  | VP | 40 |  |
| 4. | MMA | 52 | The polymer film shows a swelling of 12.1% attained in 30 min and remains same till 120 min. |
|  | BuMA | 37 |  |
|  | VP | 11 |  |
| 5. | MMA | 50 | The polymer shows a swelling of 30% attained in 30 min and it remains in a deformed shape till 120 min. |
|  | BuMA | 37 |  |
|  | DMAEMA | 13 |  |
| 6. | MMA | 39 | The polymer film shows a equilibrium swelling of 14.8% attained in 15 min and remains same till 120 min. |
|  | BuMA | 23 |  |
|  | PEMA | 38 |  |
| 7 | MMA | 41 | The edges of the polymer film start thinning and there is some swelling in 15 min. The film solubilizes almost completely in 30 min and entirely in 60 min. |
|  | HEMA | 32 |  |
|  | VP | 27 |  |
| 8. | MMA | 49 | The edges of the polymer film start to thin from the sides and the film shows high swelling in 20 min and then solubilizes in 30-40 min. |
|  | HEMA | 34 |  |
|  | DMAEMA | 17 |  |
| 9. | MMA | 39 | The polymer film shows high swelling in 15 min and it solubilizes in 30 min completely. |
|  | HEMA | 28 |  |
|  | PEMA | 33 |  |
| 10 | MMA | 47 | The polymer film solubilized in 15 min. |
|  | HEEMA | 32 |  |
|  | VP | 21 |  |
| 11 | MMA | 49 | The polymer film solubilized in 15 min. |
|  | HEEMA | 38 |  |
|  | DMAEMA | 13 |  |
| 12. | MMA | 49 | The polymer film solubilized in 15 min. |
|  | HEEMA | 27 |  |
|  | PEMA | 24 |  |

Where:
MMA = methyl methacrylate,
BuMA = butyl methacrylate,
DMAEMA = dimethyl aminoethyl methacrylate,
HEMA = hydroxy ethyl methacrylate,
VP = vinyl pyridine,
HEEMA = hydroxyethyl ethyl methacrylate,
PEMA = piperidine ethyl methacrylate

TABLE 5

Swelling/Solubility of polymer in buffer pH 4.5

| Polymer No | Composition | Monomer Weight % | Observed behavior |
|---|---|---|---|
| 1. | MMA | 83 | The polymer film does not show any swelling on the first day. The film shows slow solubilization on day 2 of 1.43% and reaching a solubilization of 12% on day 7 |
|  | VP | 17 |  |
| 2. | MMA | 75 | The polymer film goes in solution in 2 hrs on day 1. |
|  | DMAEMA | 25 |  |
| 3. | BuMA | 60 | The polymer film does not show any swelling from day 1 to day 7. |
|  | VP | 40 |  |
| 4. | MMA | 52 | The polymer film does not show any swelling from day 1 to day 7. |
|  | BuMA | 37 |  |
|  | VP | 11 |  |
| 5. | MMA | 50 | The polymer does not show any swelling in 2 hrs on day 1 but swells upto 33.3 on day 3 and it solubilizes from day 4 onwards to 11% on day 7. |
|  | BuMA | 37 |  |
|  | DMAEMA | 13 |  |
| 6. | MMA | 39 | The polymer film does not show swelling till day 3 but starts to solubilize 1.4% on day 4, 3% on day 7. |
|  | BuMA | 23 |  |
|  | PEMA | 38 |  |
| 7 | MMA | 41 | The polymer film does not show swelling on day 1 till day 3 but solubilizes 6% on day 7. |
|  | HEMA | 32 |  |
|  | VP | 27 |  |
| 8. | MMA | 49 | The polymer film swells and deforms on day 1 and goes into solution on day 2. |
|  | HEMA | 34 |  |
|  | DMAEMA | 17 |  |
| 9. | MMA | 39 | The polymer film does not show any swelling on day 1 but swells upto 10.2% on day 5 and it goes into solution 6.9% on day 7. |
|  | HEMA | 28 |  |
|  | PEMA | 33 |  |
| 10 | MMA | 47 | The polymer film shows high swelling 49% in one hr on day 1 and later deformation in shape and the film goes into solution with complete dissolution on day 5. |
|  | HEEMA | 32 |  |
|  | VP | 21 |  |
| 11 | MMA | 49 | The polymer film goes into solution partially, in one hour and complete dissolution in second hour on day 1. |
|  | HEEMA | 38 |  |
|  | DMAEMA | 13 |  |
| 12. | MMA | 49 | The polymer film shows high swelling and deformation in shape in one hour on day 1 and goes in to solution on day 2. |
|  | HEEMA | 27 |  |
|  | PEMA | 24 |  |

Where:
MMA = methyl methacrylate,
BuMA = butyl methacrylate,
DMAEMA = dimethyl aminoethyl methacrylate,
HEMA = hydroxy ethyl methacrylate,
VP = vinyl pyridine,
HEEMA = hydroxyethyl ethyl methacrylate,
PEMA = piperidine ethyl methacrylate

TABLE 6

Swelling/Solubility behavior of polymer in buffer pH 5.8

| No. | Polymer Composition | Monomer Weight % | Observed behavior |
|---|---|---|---|
| 1. | MMA<br>VP | 82<br>17 | The polymer film did not show any swelling in 2 hr on day 1 and it swelled to 3.82% on day 2 and started to solubilize with 5% on day 4 and further to 12% on day 7 |
| 2. | MMA<br>DMAEMA | 75<br>25 | The polymer film showed a swelling of 6.2% in one hour followed by solubilization of 1.6% in second hour on day 1 and it broke into pieces on day 2 and solubilized on day 4 |
| 3. | BuMA<br>VP | 60<br>40 | The polymer film does not show any swelling from day 1 to day 7. |
| 4. | MMA<br>BuMA<br>VP | 52<br>37<br>11 | The polymer film does not show any swelling from day 1 to day 7. |
| 5. | MMA<br>BuMA<br>DMAEMA | 50<br>37<br>13 | The polymer film does not show swelling on day 1 but swells up to 4.3% on day 7. |
| 6. | MMA<br>BuMA<br>PEMA | 39<br>23<br>38 | The polymer film does not show any swelling from day 1 to day 7. |
| 7 | MMA<br>HEMA<br>VP | 41<br>32<br>27 | The polymer film does not show any swelling till day 5 but swells to 1.3% on day 7. |
| 8. | MMA<br>HEMA<br>DMAEMA | 49<br>34<br>17 | The polymer film swells on day 1 and it breaks into pieces on the second day and solubilizes on day 3. |
| 9. | MMA<br>HEMA<br>PEMA | 39<br>28<br>33 | The polymer film does not show swelling till 2 days but later it swells and gets completely deformed. The polymer does not dissolve in 7 days. |
| 10 | MMA<br>HEEMA<br>VP | 47<br>32<br>21 | The polymer film shows a swelling of 41.28% in one hr. on day 1 and later it gets deformed in shape and it remains as such till day 7. |
| 11 | MMA<br>HEEMA<br>DMAEMA | 49<br>38<br>13 | The polymer film goes in solution in 2 hrs on day 1. |
| 12. | MMA<br>HEEMA<br>PEMA | 49<br>27<br>24 | The polymer film shows a high swelling and deformation on day 1 in 2 hrs and the polymer solubilizes partially till day 7. |

Where:
MMA = methyl methacrylate,
BuMA = butyl methacrylate,
DMAEMA = dimethyl aminoethyl methacrylate,
HEMA = hydroxy ethyl methacrylate,
VP = vinyl pyridine,
HEEMA = hydroxyethyl ethyl methacrylate,
PEMA = piperidine ethyl methacrylate The pH sensitive polymers, which swelled or solubilized in the acidic pH of 1.2 and remained, deswelled in the pH 5.8, were considered useful for the taste masking application. Further the polymers, which remain insoluble and have very low swelling in the pH 4.5 and 5.8, can be useful in the taste masking application of the liquid oral preparation. The polymers which are soluble in the acidic pH and which remain deswelled or show a slow swelling in the pH 4.5 and pH 5.8 can be of use for the delivery systems like film coated tablets and rapidly disintegrating and chewable tablets where the polymer has to provide the taste masking for a short period of time till the transit of the drug from oral cavity to stomach.

The Advantages of the Present Invention are as Follows:
1) The pH sensitive polymers described herein can be used for the pharmaceutical applications particularly the delivery of the drugs in the gastric region.
2) The pH sensitive polymer swells or solubilizes at the acidic pH of stomach. It can release the drug almost immediately in the gastric region, without causing any delay.
3) Since the pH sensitive polymer releases the drug in gastric region almost immediately, there would be no alteration in the bioavailability of the drugs that have a narrow absorption window restricted to the upper gastric region.
4) The pH sensitive polymer can be used for taste masking applications since the polymer remains deswelled in the pH of the saliva and also in the reconstitution medium as in case of liquid oral pharmaceutical preparations.
5) The pH sensitive polymer can be used in a variety of dosage forms like the film coating of the tablets, coating of bitter particles of the drugs to be formulated as dry syrups, suspension and chewable or rapidly disintegrating tablets where taste masking is required.
6) Apart from taste masking, the pH sensitive polymers can provide the moisture barrier to the sensitive moieties since they are insoluble in water and hydrophobic in nature.

We claim:

1. A polymer which is soluble at pH≦3.5, having a general formula $$P[A_{(x)}B_{(y)}C_{(z)}]$$

wherein P is a pH sensitive polymer comprising (A) a hydrophobic monomer, (B) a basic monomer which is 4-vinyl pyridine, and (C) a hydrophilic monomer and (x)=30-65%, (y)=5-45%, and (z)=10-45%, all percentages expressed in terms of weight by weight of the polymer (w/w).

2. A polymer as claimed in claim 1 wherein the hydrophobic monomer (A) comprises an acrylic acid derivative selected from the group consisting of cyclohexyl acrylate, dodecyl acrylate, 2-ethyl hexyl acrylate, octyl acrylate, tertiary butyl acrylate, phenyl acrylate, and butyl acrylate.

3. A polymer as claimed in claim 1 wherein the hydrophobic monomer (A) comprises a methacrylic acid derivative selected from the group consisting of methyl methacrylate, benzyl methacrylate, cyclohexyl methacrylate, phenyl methacrylate, tertiary butyl methacrylate, butyl methacrylate, 2-ethyl hexyl methacrylate, and propyl methacrylate.

4. A polymer as claimed in claim 1 wherein the hydrophobic monomer (A) comprises a derivative of acrylic or methacrylic acid.

5. A polymer as claimed in claim 1 wherein the hydrophilic monomer (C) comprises a derivative of methacrylic acid selected from the group consisting of hydroxy ethyl methacrylate and hydroxy propyl methacrylate.

6. A polymer as claimed in claim 5 wherein the hydrophilic monomer (C) comprises hydroxy ethyl methacrylate.

7. A polymer as claimed in claim 1 wherein the pH sensitive polymer has a molecular weight in the range of 1000 to 7,00,000.

8. A polymer as claimed in claim 1 wherein the pH sensitive polymer is insoluble in water.

* * * * *